United States Patent [19]

Nakao et al.

[11] 4,070,244

[45] Jan. 24, 1978

[54] METHOD FOR PRODUCING UBIQUINONE-10

[75] Inventors: Yoshio Nakao, Ibaraki; Kazuaki Kitano, Suita; Isuke Imada, Izumi; Hiroshi Morimoto, Nishinomiya, all of Japan

[73] Assignee: Takeda Chemical Industries, Ltd., Osaka, Japan

[21] Appl. No.: 772,332

[22] Filed: Feb. 25, 1977

[30] Foreign Application Priority Data

Feb. 27, 1976 Japan .................................. 51-21513

[51] Int. Cl.$^2$ ............................................ C12D 13/02
[52] U.S. Cl. ..................................................... 195/81

[58] Field of Search .......................................... 195/81

[56] References Cited
PUBLICATIONS

McCormick et al., Methods in Enzymology, vol. XVIII, Part C, pp. 141 & 216–226 (1971).

Primary Examiner—Alvin E. Tanenholtz
Attorney, Agent, or Firm—Wenderoth, Lind & Ponack

[57] ABSTRACT

Ubiquinone-10 is produced by culturing a microorganism belonging to the genus *Sporidiobolus* or *Oosporidium* and capable of producing ubiquinone-10, causing the microorganism to accumulate ubiquinone-10 and recovering ubiquinone-10.

11 Claims, No Drawings

METHOD FOR PRODUCING UBIQUINONE-10

This invention relates to a method for producing ubiquinone-10 which comprises cultivating a ubiquinone-10-producing microorganism of the genus *Sporidiobolus* or of the genus *Oosporidium* and separating ubiquinone-10 from the microbial cells.

Ubiquinone is a generic designation for a series of compounds having the general formula:

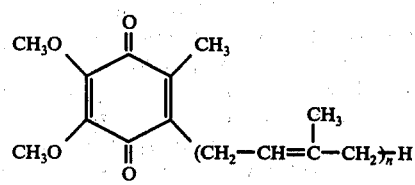

, and ubiquinone-10 is a compound of the above general formula wherein n is equal to 10, that is to say, a compound which has 10 isoprene units in the multiprenyl side chain.

Ubiquinone-10 is a physiologically important derivative of ubiquinone, which is widely distributed in the animal and vegetable kingdoms and which is involved in the terminal electron transport system of a living thing.

It has recently been reported that, like other ubiquinone homologs, this particular compound displays certain pharmacological activities such as the activity to alleviate cardiac insufficiency and certain physiological activities such as the activity to stimulate the oxidationreduction activity of myocardiac mitochondria in mammals including human beings, dogs and rats (for example, Seikagaku Zikken Koza, Vol. 13, pp. 681–682, Tokyo Kagaku Dozin, 1975). Clinically, ubiquinone-10 has been orally administered to patients with cardiac insufficiency, normally at a regular dose of 0.5 to 1 mg/kg daily for an adult human.

For the production of ubiquinone-10, a method comprising extracting the same from animal tissues is generally known. However, partly because of the limited availability of such sources and partly because the compound occurs only in meager percents, it is extremely difficult to produce ubiquinone-10 in commercially meaningful amounts on an industrial scale. It is known that certain strains of bacteria of such genera as *Pseudomonas*, *Agrobacterium*, etc., of fungi of such genera as *Neurospora*, *Aspergillus*, *Aureobasidium*, etc., of yeasts of such genera as *Rhodotorula*, *Chyptococcus*, *Candida*, *Torulopsis*, *Trichosporon*, *Sporobolomyces*, *Bullera*, *Rhodosporidium*, *Schizosaccharomyces*, etc. and of basidiomycetes of such genera as *Tremella* are capable of accumulating ubiquinone-10 in their cells. Nevertheless, because of the inadequate amount of ubiquinone-10 that is accumulated in the cells, among other reasons, no commercial method has yet been established that makes avail of these organisms.

That is to say, in case of bacteria, firstly the cells tend to be infected by bacteriophages and to lose the cell activities in the course of fermentation and secondly collecting of the cells by centrifugation or filtration is difficult and takes long time because of its minuteness.

On the other hand, in cases of yeast, fungi and basidiomycetes, the yield of ubiquinone-10 is not satisfactory.

Against the above background we did an extensive research into the possibility of developing a commercially profitable method of producing ubiquinone-10.

The research led us to the finding that certain microorganisms belonging to the genus *Sporidiobolus* or the genus *Oosporidum*, none of which microorganisms had been known to produce ubiquinone-10, were able to accumulate ubiquinone-10 intracellularly in a large amount. The finding was followed by further studies which have led into the present invention.

Therefore, the present invention relates to a microbial method of producing ubiquinone-10 characterized in that said method comprises cultivating a microorganism of the genus *Sporidiobolus* or of the genus *Oosporidium*, said microorganism being able to produce ubiquinone-10, and harvesting the same product.

In accordance with the present invention, any of the strains of the genus *Sporidiobolus* or the genus *Oosporidium* which are able to produce ubiquinone-10 may be employed with advantage in an appropriate manner. Thus, among the stains which may be advantageously used are *Sporidiobolus johnsonii* IFO-6903 (ATCC-20490) and *Sporidiobolus ruinenii* CBS-5001 (IFO-1689, ATCC-20489), *Oosporidium margaritiferum* CBS-2531 (ATCC-10676, IFO-1208) and *Oosporidium margaritiferum* CBS-6177 (IFO-1688), and to name but a few. These strains of microorganisms have been deposited at Centraal Bureau voor Schimmelcultures (CBS), Holland; The Institute for Fermentation, Osaka (IFO), Japan; or The American Type Culture Collection (ATCC), Maryland, U.S.A. under the numbers mentioned above.

It is to be noted that pertinent descriptions of CBS-2531 and CBS-6177 appear in CBS List of Cultures, 28th ed. (1972) on page 305; IFO-6903 is described in IFO List of Cultures, 5th ed. (1972) on page 181; and a description of CBS-5001 is found in Lodder, The Yeasts, 2nd ed., on pages 827–830.

The cultivation of such microorganisms exploited according to the present invention may be carried out using a suitable medium containing assimilable carbon sources, digestable nitrogen sources, inorganic salts, vitamins and so forth. The carbon sources may be any materials which the microorganisms employed may assimilate, including carbohydrates (e.g. glucose, sucrose, maltose, dextrin, soluble starch, starch, molassess, etc.), glycerin, oils and fats (e.g. olive oil, rice bran oil, etc.), organic acids (e.g. acetic acid, lactic acid, fumaric acid, succinic acid, citric acid, etc.), alcohols (e.g. ethanol, propanol, etc.), other sources. As said nitrogen sources may be mentioned, among others, malt extract, peptone, soybean extract, meat extract, yeast extract, corn steep liquor, urea, ammonium salts (e.g. ammonium sulfate, ammonium chloride, etc.), nitrates (e.g. ammonium nitrate, sodium nitrate, etc.), and other organic and inorganic nitrogenous materials. If necessary, there may also be added suitable amounts of inorganic salts (e.g. sodium chloride, phosphates, etc.), metal salts (the sulfates, hydrochlorides, nitrates and other salts of calcium, magnesium, manganese, iron, etc.), trace nutrients (e.g. vitamins, amino acids, nucleotides, etc.), other enhancing substances (e.g. p-hydroxybenzoic acid, chorismic acid, shikimic acid, etc.) and so on, especially an addition of an least 10 μg/l, preferably 1000 μg/l to 30000 μg/l of p-hydroxybenzoic acid is more effective to increase the yield of the objective compound. And salts (e.g. sodium salt, potassium salt, etc.) of p-hydroxybenzoic acid and fatty acid esters (e.g. ethylester, n-nonylester, laurylester, etc.) of p-hydroxybenzoic acid are also employable.

While whichever of stationary and shake cultural methods may be employed, submerged culture under aerobic conditions is generally advantageous. Generally the incubation temperature is desirably in the range of 15° to 40° C and, with the pH of the medium being held within the range of 2 to 10 and, preferably within the range of 3 to 8, cultivation is desirably continued for about 10 hours to about 10 days. From the resultant broth, the cells are separated and recovered by such procedures as centrifugation of filtration. Because ubiquinone-10 is rich in the cell thus harvested, the cells may, after appropriate processing (for example, drying, milling, etc.), be used directly as a nutritive agent of a pharmaceutical agent. If necessary, ubiquinone-10 may be isolated from the cellular product.

The isolation of ubiquinone-10 from the cells may be accomplished in a manner conventional per se. Ubiquinone- 10 is a neutral liqid. Namely it is insoluble in water, soluble in polar organic solvents and freely soluble in nonpolar solvents particularly hydrocarbons. The isolation is conducted by utilizing the above characteristics. The following is a typical isolation method of ubiquinone-10. The cells are added to ethanol and extracted under heating at 50° to 90° C for one to several hours. Alternatively, the phospholipids and other saponifiable components of the cells are first saponified with a mixture of methanol, sodium hydroxide and pyrogallol and, then, a water-immiscible solvent such as n-hexane is added to the saponified fluid so as to extract the ubiquinone-10. Thereafter, the extract may be subjected to a fractional purification procedure using silica gel or Florisil (Floridin Co. U.S.A.) for instance, to isolate the same compound.

The identity of ubiquinone-10 thus extracted from the cells may be established by paper chromatography, thinlayer chromatography, elemental analysis, melting point determination, infrared and ultraviolet absorption spectrometry, nuclear magnetic resonance spectrometry, mass spectrometry and other methods.

Quantitative determinations may be made, for example, by Redfarn's method (Methods in Enzymology, Vol. 10, p.381 (1967).

The following examples are further illustrative but by no means limitative of the invention, wherein "part(s)" is based on weight unless otherwise noted and the relationship between "part(s)" and "part(s) by volume" corresponds to that between "gram(s)" and "milliliter(s)," and "%" is based on weight/volume unless otherwise noted.

EXAMPLE 1

A small fermentation tank (5000 parts by volume capacity) was charged with 3000 parts by volume of a culture medium (pH 6.0) comprising 3% glucose, 1% polypepton, 0.5% yeast extract and 0.5% malt extract. The medium was sterilized by heating in a conventional manner and cooled. This medium was inoculated with 150 parts by volume of a pre-culture of *Sporidiobolus ruinenii* CBS-5001, which had been prepared by growing the same strain on a medium of the same composition as above at 28° C for one day. The inoculated medium was incubated at 28° C and under agitation at 800 r.p.m. with sparging at a rate of 3000 parts by volume per minute for 24 hours. During this fermentation period, the medium was maintained at pH 6.0 with ammonia and sulfuric acid.

The resultant fermentation broth was centrifuged to harvest the microbial cells, and they were washed with water and centrifuged a second time, whereupon a living cell paste was obtained (There was obtained an amount of cells equivalent to 54 parts on a dry basis, which contained 920 $\mu$g of ubiquinone-10 per gram of dry cells).

The moist cells were suspended in 750 parts of volume of ethanol and extracted by warming at 60° C for 1 hour. A total of 3 extractions were carried out in a similar manner and the extracts were pooled, diluted with water and further extracted three times with 1000 parts of volume portions of n-hexane. The n-hexane layer was concentrated to dryness under reduced pressure to recover 4.12 parts of a yellow oil. This oily residue was dissolved in 6 parts by volume of benzene and passed through a column (500 parts by volume capacity) packed with Floridil (100 to 200 meshes). Elution was carried out using benzene and the eluate was collected in 10 parts by volume fractions. Each fraction was analyzed by thin-layer chromatography and color reaction and the fractions rich in ubiquinone-10 were pooled and concentrated under reduced pressure. By this procedure was obtained 0.562 part of a yellow oil. This product was dissolved in 5 parts by volume of chloroform, coated onto a thin layer plate of silica gel GF254 (silica gel with calcium sulfate) and developed with benzene. The fractions corresponding to ubiquinone-10 were extracted, whereby 0.054 part of a yellow oil was obtained. This oil was dissolved in 10 parts by volume of ethanol and allowed to cool, whereupon 0.029 part of yellow crystals of ubiquinone-10 were obtained. Its physical properties - melting point 48° to 50° C, UV ($\lambda$max/ethanol 275 nm) and mass spectrum (m/e, $M^+$862, hydroquinone form 864, pyrylium ion peak 235, benzylium ion peak 197) - showed that the oily product was identical with ubiquinone-10.

EXAMPLE 2

By a procedure similar to that set forth in Example 1, *Sporidiobolus johnsonii* IFO-6903 was cultivated to obtain a live cell paste (45 parts on a dry basis). The cells contained 520 $\mu$g of ubiquinone-10 per gram of a dry basis. The cells were treated in the same manner as Example 1 to obtain 13.6 $\times$ $10^{-3}$ part of yellow crystals of ubiquinone-10. The identification of the product was carried out by procedures similar to those described in Example I.

EXAMPLE 3

30 parts by volume aliquots of a medium of the same composition as described in Example 1 was distributed into 200 parts by volume flasks and sterilized. Each flask was inoculated with a loopful of *Oosporidium margaritiferum* CBS-2531 and incubated at 24° C for one week. 1620 parts by volume of the incubated culture broth are collected. The cells were harvested from the broth. The above procedure yielded 169 parts of moist cells (corresponding to 41 parts of dry cells) containing 450 $\mu$g of ubiquinone-10 per gram on a dry basis. The cells were treated as in Example 1 to give 4.47 parts of a yellow oily product. This product was further treated as in Example 1 to obtain 11 $\times$ $10^{-3}$ part of yellow crystals of ubiquinone-10. The identification of the product was performed as in Example 1.

EXAMPLE 4

By a procedure similar to that described in Example 3, *Oosporidium margaritiferum* CBS-6177 was cultivated to obtain 1020 parts by volume of the incubated culture broth. The cells were harvested from the broth. The above procedure yielded 120 parts of moist cells (corresponding to 25 parts dry cells) containing 550 μg of ubiquinone-10 per gram on a dry basis. The cells were further treated as in Example 1 to obtain $5.6 \times 10^{-3}$ part of yellow crystals of ubiquinone-10. The identification of this product with ubiquinone-10 was carried out in a similar manner as in Example 1.

EXAMPLE 5

A fermentor of 200 parts by volume was charged with 30 parts by volume of a culture medium (pH 6.0) comprising 3% glucose, 1% polypepton, 0.5% yeast extract and 0.5% malt extract. The medium was sterilized by heating in a conventional manner and cooled. This medium was inoculated with *Sporidiobolus johnsonii* IFO 6903. The inoculated medium was incubated at 28° C for 48 hours under agitation to give a seed culture.

A fermentation tank (5000 parts by volume) was charged with 3000 parts by volume of a culture medium comprising 6% glucose, 0.3% dried yeast, 0.12% KCl, 0.1% $MgSO_4$, 0.02% $FeSO_4$, 0.2% $(NH_4)_2SO_4$, 0.5% urea, 0.015% $CaCl_2$, 0.25% $H_3PO_4$, 0.002% $ZnSO_4$, 0.001% $MnSO_4$, 0.0005% $CuSO_4$, $5 \times 10^{-5}\%$ vitamin $B_1$, $5 \times 10^{-4}\%$ p-hydroxybenzoic acid. The medium was sterilized by heating in a conventional manner and cooled.

This medium was inoculated with 150 parts by volume of said seed culture, and the inoculated medium was incubated at 28° C for 21 hours under agitation at 800 r.p.m. with sparging at a rate of 3000 parts by volume per minutes. During this fermentation period, the medium was maintained at pH 6.0 with ammonia and sulfuric acid.

The resultant fermentation broth was filtered to harvest the microbial cells.

The above procedure yielded 380 parts of moist cells (corresponding to 84 parts of dry cells) containing 740 μg. of ubiquinone-10 per gram on a dry basis.

The cells were treated as in Example 1 to give 0.038 part of crystals of ubiquinone-10.

EXAMPLE 6

A fermenter (200 parts by volume capacity) was charged with 30 parts by volume of a culture medium (pH 6.0) comprising 6% glucose, 0.5% yeast extract, 0.12% KCl, 0.1% $MgSO_4$, 0.02% $FeSO_4$, 0.3% $(NH_4)_2SO_4$, 0.3% urea, 0.15% $H_3PO_4$, 0.002% $ZnSO_4$, 0.001% $MnSO_4$, 0.0005% $CuSO_4$ $5 \times 10^{-5}\%$ vitamin $B_1$, $5 \times 10^{-4}\%$ p-hydroxybenzoic acid and 0.3% $CaCO_3$. The medium was sterilized by heating in a conventional manner and cooled. This medium was inoculated with *Oosporidium margaritiferum* CBS-2531. The inoculated medium was incubated at 24° C for 144 hours.

Two thousand and ten parts of the resultant fermentation broth was filtered to harvest the microbial cells.

The above procedure yielded 250 parts of moist cells (corresponding to 40 parts of dry cells) containing 760 μg. of ubiquinone-10 per gram on a dry basis.

The cells were treated as in Example 1 to give 0.022 part of yellow crystals of ubiquinone-10.

EXAMPLE 7

By a procedure similar to that described in Example 6, *Oosporidium margaritiferum* CBS-6177 was cultivated to obtain 210 parts of moist cells (corresponding to 43 part of dry cells) containing 750 μg. of ubiquinone-10 per gram on a dry basis.

The cells were treated as in Example 1 to give 0.02 part of yellow crystals of ubiquinone-10.

What we claim is:

1. A method for producing ubiquinone-10 which comprises; cultivating a microorganism which belongs to the genus *Sporidiobolus* or the genus *Oosporidium* and is capable of producing ubiquinone-10 in a culture medium containing an assimilable carbon source and a digestible nitrogen source until ubiquinone-10 is substantially accumulated; and recovering ubiquinone-10.

2. A method according to claim 1, wherein the microorganism belongs to the genus *Sporidiobolus*.

3. A method according to claim 1, wherein the microorganism belongs to the genus *Oosporidium*.

4. A method according to claim 1, wherein the medium contains p-hydroxybenzoic acid.

5. A method according to claim 2, wherein the microorganism is *Sporidiobolus johnsonii*.

6. A method according to claim 2, wherein the microorganism is *Sporidiobolus ruinenii*.

7. A method according to claim 3, wherein the microorganism is *Oosporidium margaritiferum*.

8. A method according to claim 5, wherein the microorganism is *Sporidiobolus johnsonii* IFO-6903.

9. A method according to claim 6, wherein the microorganism is *Sporidiobolus ruinenii* CBS-5001.

10. A method according to claim 7, wherein the microorganism is *Oosporidium margaritiferum* CBS-2531.

11. A method according to claim 7, wherein the microorganism is *Oosporidium margaritiferum* CBS-6177.

* * * * *